(12) United States Patent
Jiao et al.

(10) Patent No.: US 9,139,550 B2
(45) Date of Patent: Sep. 22, 2015

(54) FLUORESCENCE DYE TAGGING SCHEME FOR MERCURY QUANTIFICATION AND SPECIATION

(75) Inventors: Hong Jiao, Santa Clara, CA (US); Hannah Catterall, San Jose, CA (US)

(73) Assignee: Los Gatos Research, Mountain View, CA (US)

( * ) Notice: Subject to any disclaimer, the term of this patent is extended or adjusted under 35 U.S.C. 154(b) by 561 days.

(21) Appl. No.: 13/570,548

(22) Filed: Aug. 9, 2012

(65) Prior Publication Data

US 2013/0040393 A1 Feb. 14, 2013

Related U.S. Application Data

(60) Provisional application No. 61/521,611, filed on Aug. 9, 2011.

(51) Int. Cl.
*G01N 21/64* (2006.01)
*G01N 33/84* (2006.01)
*C07D 311/18* (2006.01)
*C07D 405/12* (2006.01)

(52) U.S. Cl.
CPC ............ *C07D 311/18* (2013.01); *C07D 405/12* (2013.01)

(58) Field of Classification Search
CPC .............. G01N 33/0045; G01N 31/22; G01N 33/1813; G01N 21/64; G01N 21/3103; G01N 33/84
USPC ........................................................ 436/81
See application file for complete search history.

(56) References Cited

U.S. PATENT DOCUMENTS

| | | | |
|---|---|---|---|
| 5,733,786 A * | 3/1998 | Green | ............................. 436/81 |
| 8,058,075 B2 | 11/2011 | Zang et al. | |
| 8,062,893 B2 | 11/2011 | Wang et al. | |
| 8,158,801 B2 | 4/2012 | Buller et al. | |
| 2006/0051878 A1* | 3/2006 | Dickson et al. | ................ 436/518 |

OTHER PUBLICATIONS

Enhanced Amine and Amino Acid Analysis Using Pacific Blue and the Mars Organic Analyzer Microchip Capillary Electrophoresis System Thomas N. Chiesl, Wak K. Chu, Amanda M. Stockton, Xenia Amashukeli, Frank Grunthaner, and Richard A. Mathies Anal. Chem. 2009, 81.*
T.N. Chiesl et al., "Enhanced amine and amino acid analysis using pacific blue and the mars organic analyzer microchip capillary electrophoresis system", Anal. Chem. 2009, Apr. 1, 2009, vol. 81, No. 7, pp. 2537-2544.
A.M. Stockton et al., "Capillary electrophoresis analysis of organic amines and amino acids in saline and acidic samples using the mars organic analyzer", Astrobiology, 2009, vol. 9, No. 9, pp. 823-831.

(Continued)

*Primary Examiner* — Krishnan S Menon
*Assistant Examiner* — Dwan A Gerido
(74) *Attorney, Agent, or Firm* — Thomas Schneck; Mark Protsik

(57) ABSTRACT

A fluorescent dye or fluorophore capable of forming complexes with mercury comprises 6,8-difluoro-7-hydroxy-2-oxo-2H-chromene-3-carboxylate amide, wherein the amide is formed by reacting the succinimidyl ester (Pacific Blue™) with an amino acid containing a thiol group, such as cysteine or glutathione. Mercury complexes of the fluorophore fluoresce when excited by a UV or violet laser diode, and the detected intensity can be calibrated to quantify the concentration of mercury in a sample reacted with the fluorophore.

6 Claims, 3 Drawing Sheets

(56) References Cited

OTHER PUBLICATIONS

M.P. Mora et al., "Toward automation of microfluidics for extraterrestial in situ analysis", Anal. Chem., Nov. 15, 2011, vol. 83, No. 22, pp. 8636-8641.

Book: "Handbook of capillary and microchip electrophoresis and associated microtechniques", 3rd edition, Edited by J. P. Landers, CRC Press 2007, 18 pages. (contents & references).
Relevant Chapter 46 of book: C.A. Emrich et al., "Microfabricated electrophoresis devices for high-throughput genetic analysis: milestones and challenges", pp. 1277-1295, 2008.

* cited by examiner

FLUORESCENCE DYE TAGGING SCHEME FOR MERCURY QUANTIFICATION AND SPECIATION

CROSS-REFERENCE TO RELATED APPLICATION

This application claims priority under 35 U.S.C. 119(e) from U.S. Provisional Patent Application 61/521,611, filed Aug. 9, 2011.

STATEMENT REGARDING FEDERALLY-SPONSORED RESEARCH AND DEVELOPMENT

This invention was made with government support under contract number DE-SC0004430 awarded by the Department of Energy. The government has certain rights in the invention.

TECHNICAL FIELD

The present invention relates to optical measuring and testing for analytical chemistry, namely using optically excited fluorescence for measuring samples for the quantity of mercury of various species that may be present in such samples, and relates in particular to fluorescent dyes or fluorophores that are particularly adapted to the tagging of mercury and its compounds.

BACKGROUND ART

Many different types of contaminants are present in polluted groundwater and soil. The potential for humans or sensitive ecosystems to be exposed to such contaminants is strongly affected by a number of factors. Because speciation controls the environmental transport and risks of these contaminants, it is important to measure not only the contaminant concentration, but also its oxidation state.

Mercury is of particular concern because it is a highly toxic element that is widely disseminated throughout the atmosphere and hydrosphere. Additionally, the toxicity, biochemical behavior, and bioavailability of mercury are strongly dependent on the chemical form of the element. Among the three common forms of mercury: elemental mercury)($Hg^0$), ionic mercury (He), and organic mercury complexes (methylmercury, ethylmercury, phenylmercury, etc.), methylmercury ($CH_3Hg^{2+}$) is the most toxic and abundant form of mercury found in the environment. Depending on environmental conditions, mercury can also transform among the different forms, so the existence of any form of mercury is potentially harmful to human health.

Natural mercury emissions have led to the distribution of mercury throughout the environment via volcanoes, fires, rivers, and biological processes. Off-gassing of mercury from the lithosphere and hydrosphere to the atmosphere results in the deposition of mercury in aquatic and terrestrial environments.

In addition to natural mercury emissions, industrial activities (e.g. coal mining, silver mining, burning of fossil fuels, and other industrial processes) have created new mercury emission pathways to various sites in the environment. Approximately 80% of anthropogenic mercury emissions release elemental mercury) ($Hg^0$) into the air through industrial processes. Meanwhile, almost 15% of this mercury is released into the terrestrial environment. The final 5% of anthropogenic mercury emissions is transported from industrial wastewater to the aquatic environment. A total estimate of 4,700 tons of mercury is released from human-related activities each year to deposit in the environment. Deposited mercury can then re-emit into the atmosphere by biological and geological means.

Concentrated mercury, especially methylmercury, poses serious problems to human health, as bioaccumulation of mercury within the brain and kidneys ultimately leads to neurological diseases. Therefore, mercury monitoring and mercury speciation are important for the environment and human health.

SUMMARY OF CURRENT TECHNOLOGY

A wide variety of instrumental methods have been developed for the determination of environmental mercury, including biosensors, chemical sensors, conductometric and microcantilever sensors, nanosensors, surface acoustic wave (SAW) sensors, and piezoelectric sensors. However, most commercially available portable units employ either a gold film technique or atomic absorption spectrometry (AAS).

In the gold film method, gold film inside an instrument absorbs mercury and the resulting change in electrical conductivity is measured. These systems respond only to mercury and are not subject to hydrocarbon or moisture interferences. However, gold film sensors must be regenerated often by first heating the film to drive off the absorbed mercury vapor and the reconditioning it for use. Moreover, gold film techniques lack the detection sensitivities that are achieved in a laboratory instrument.

In AAS, mercury concentration is measured via direct UV absorption in conjunction with a spectrometer. When used with cold vapor atomic absorption spectrometry (CVAAS), the method provides high sensitivities for monitoring trace amounts of mercury in the environment. Since all of these techniques change the oxidation state of the measured mercury, none of these techniques alone are capable of mercury speciation.

In order to identify different forms of mercury via mercury speciation, it is necessary to use a chromatography to separate out the different mercury compounds. This is traditionally based on either gas chromatography (GC) or high performance liquid chromatography (HPLC). The measurement of mercury as it elutes from the column uses elemental detection methods, such as inductively-coupled plasma/mass spectrometry (ICP-MS) or cold-vapor atomic absorption/fluorescence spectrometry (CVAAS/CVAFS). While many of these methods are capable of determining sub-ppt concentrations of mercury and its chemical forms, they all suffer the drawback of having to take the samples from the field to the laboratory for analysis, which is time consuming, expensive, and dangerous (e.g. possible exposure of personnel to hazardous contaminants).

Few of the current commercial instruments are completely integrated. The vendors typically supply the stand-alone detectors (CVAFS, CVAAS, ICP-MS, etc.), and the users must adapt their own separation devices (GC, HPLC, etc.). Additionally, all commercial laboratory analytical instruments for performing mercury speciation consist of several bulky units: stand-alone detection assembly, isocratic high pressure pump, manual injection valve and solvent cabinet, a suitable Agilent or Dionex HPLC column, and a PC. The combined laboratory instrumentation, therefore, has a huge footprint as well as huge power consumption. As a result, current commercially available laboratory based analyzers capable of performing mercury speciation are all ill-suited for field deployable on-site applications.

In order to address this issue, researchers are developing micro-separation techniques that can be readily field-deployed (e.g. micro-HPLC, micro capillary electrophoresis) and integrated into lab-on-a-chip sensors. In order to miniaturize the entire system, on-chip detection schemes are required. Current on-chip detection techniques such as LED absorption, chemiluminescence and electrochemical detection lack the required sensitivities with the typical detection sensitivities on the orders of ppm. Confocal laser induced fluorescence (LIF) is one of the most sensitive detection methods for microchips with typical sensitivities on the order of ~0.005 ppb. Direct fluorescence with native mercury species, however, requires a bulky 253.7 nm UV laser or lamp, which is difficult for miniaturization. More importantly, this method requires all mercury species converted to the elemental $Hg^0$ form, and the fluorescence be performed in inert gas in order to avoid fluorescence quenching, clearly not a viable option for microfluidic chip.

Adapting LIF for detection of trace mercury or other metals in a microchip requires an efficient fluorophore. HQS (8-hydroxyquinoline-5-sulphonic acid), the traditional fluorophore used to complex many metal ions, requires a large frame argon ion laser which unfortunately limits its usage to a laboratory environment.

SUMMARY DISCLOSURE

We have developed an efficient fluorophore that works with a miniature commercial 405 nm laser diode as the excitation source. Therefore, a fluorescence dye tagging scheme using this fluorophore enables on-chip, miniaturized detectors for mercury quantification and speciation. By combining a miniature laser diode, a detector, optics, and electronics with a microfluidic chip that has automated on-chip sample preparation and CE analysis capability, an integrated miniature trace mercury analyzer is realized, so to fulfill stringent requirements for in-situ measurement of mercury, both in terms of metal concentration detection sensitivity and chemical speciation analysis.

In particular, our approach utilizes the formation of metal complexes in combination with an efficient fluorophore for sensitive UV laser induced fluorescence (LIF) detection so as to overcome the limitations of the current on-chip detection methods such as UV absorption, chemiluminescence, and electrochemical sensing. Mercury's affinity to thiols (—SH) allows it to form complexes in chromatography. For example, mercury ion ($Hg^{2+}$) and methylmercury ($CH_3Hg^+$) form complexes with thiols according to the following reactions, respectively:

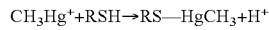

We have discovered how to conveniently "tag" a thiol with an efficient fluorophore, while preserving mercury affinity to thiols.

We have chemically modified an existing fluorophore, Pacific Blue™ succinimidyl ester (PBSE), by attaching thiol-containing amino acids, so as to optimize it for use as an efficient fluorescent probe with mercury affinity. PBSE is a fluorine-substituted benzopyran-based probe, specifically 6,8-difluoro-7-hydroxy-2-oxo-2H-chromene-3-carboxylate succinimidyl ester, with the formula $C_{14}H_7F_2NO_7$ (mol. wt. 339.2086). Compared with conventional fluorescamine, PBSE has a larger extinction coefficient (46 000 vs 7800 M-1 cm-1) and a higher fluorescence quantum yield (0.78 vs 0.11). In addition PBSE improves NHS (N-hydroxy succinimide) reaction chemistry. Reactions are performed at a slightly basic pH and occur by nucleophilic addition of a deprotonated amine to the carbonyl group of the dye. Succinimides are good leaving groups, and a molar excess of dye enables pseudo-first-order kinetics which pushes the reaction kinetics towards selective amine tagging. Amino acid derivatization with PB reaches 90% completion in approximately 15 min, and the resulting amide bond is very stable.

Of the amino acids, cysteine has a free thiol group which can form complex with inorganic mercury and methylmercury while the amine group readily reacts with PBSE. Cysteine (cys) is therefore a natural thiol choice because the amine group can be readily "tagged" with the Pacific Blue (PB) fluorescent probe, and the resulting mercury-cysteine/PB complex is optically detected by LIF with extremely high sensitivity. In accordance with the reactions above, each inorganic mercury ion ($Hg^{2+}$) forms complex with two cysteine/PB molecules whereas each methylmercury ion ($CH_3Hg^+$) forms complex with one cysteine/PB molecule. The resulting modified fluorophore is 6,8-difluoro-7-hydroxy-2-oxo-2H-chromene-3-carboxylate cysteine amide. Alternatively, glutathione is another thiol-containing amino acid that may be used instead of cysteine. The amide may be buffered to a basic pH near 9, for example in a range from 8.5 to 9.2, such as with sodium tetraborate.

The fluorescent dye may be used for measuring the mercury concentration in a sample. Combining a known quantity of a sample with a known quantity of the modified fluorophore, any mercury in the sample will react with the free thiol group to form a mercury-flourophore complex. Illuminating the complex with a laser source excites it to fluorescence. The measured intensity is indicative of the concentration of mercury in the sample (after suitable calibration using samples of known mercury quantity). The complex may be distinguished from any remaining unreacted fluorophore by a difference of fluorescence wavelength. Species of other metals that might also combine with the thiol group (e.g. cadmium) may be pre-separated by a chromatography technique. Likewise, different species of mercury contaminants, will be pre-separated and combine with the fluorophore and be detected at different time intervals.

DETAILED DESCRIPTION

Figure 1:
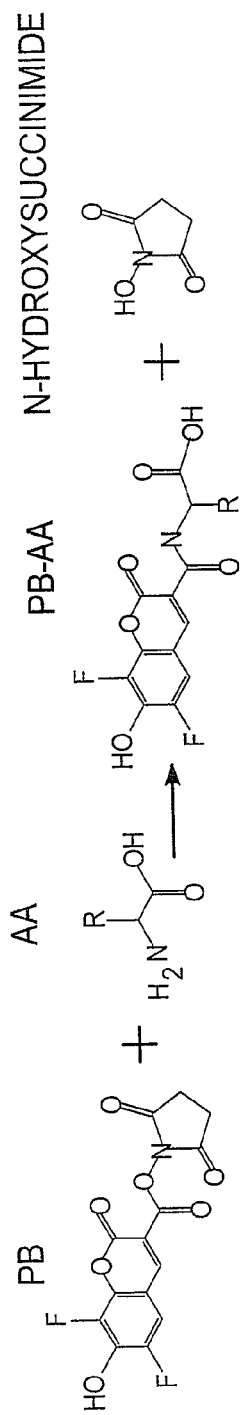
FIG. 1 illustrates a chemical reaction modifying Pacific Blue™ succinimidyl ester with a primary amine group.

A sample mercury-cysteine/PB derivatization procedure is outlined below:

1. 121.16 mg (1 mmol) of L-cysteine (Cys) (CAS [52-90-4]; Catalog #: 30089 from Sigma Aldrich) is dissolved in 10 mL of DI H2O in a Class A 10 mL volumetric flask (Sigma Aldrich) to bring the concentration to 100 mM. 5 mL of the 100 mM Cys solution is pipetted using a volumetric pipette into a 50 mL volumetric flask and brought to volume with DI H2O, for a 10 mM concentration of Cys. This is the stock solution for derivatizations.

2. 20 mM of Pacific Blue™ (PB) stock solution (Invitrogen, P10163) is prepared by dissolving 5 mg (0.01474 mM) of Pacific Blue succinimidyl ester in 737 µL of n,n-dimethyformamide (DMF) (Sigma Aldrich) using a VWR automatic pipette checked for precision in-house. The vial is mixed with a Vortex Maxi Mix II to insure uniformity in the solution. Five 50 L aliquots are auto pipetted (checked for precision in-house) into five separate amber micro centrifuge tubes which along with the remaining 487 L in the vial are stored at −20° C. in a freezer (Cole-Parmer).

3. The pH of the 5 mM sodium tetraborate ($Na_2B_4O_7$) buffer is adjusted to 8.5 by HCl solution and is checked with an electronic pH meter calibrated in-house by using purchased pH calibration buffer solutions at 7, 4.01, and 10. Cys soln (1 L), PB soln (1 L), and the buffer (498 L) are auto pipetted into a 1.5 mL micro centrifuge tube. The reaction mixture is manually held on a Vortex Maxi Mix II on high power for 3-5 sec. The vial is then placed in a micro tube rack and attached to the Maxi Mix II and stirred at low/medium speed for 2 hours at room temperature. The 20 M solution is used to make all subsequent dilutions.

4. All dilutions are made using automatic pipettes checked for precision in house. The $Na_2B_4O_7$ buffer is used to bring the solutions to volume. The solutions are stored at 5° C. when not in use in order to increase the shelf life of the derivatized amino acids. When stored in such a manner, the derivatized amino acids are good for about a week.

5. 2.7 mg (0.01 mmol) of mercury (II) chloride ($HgCl_2$) (CAS [7487-94-7]; Catalog #: 42972 from Sigma Aldrich) is dissolved in 10 mL of methanol in a Class A 10 mL volumetric flask (Sigma Aldrich) to bring the concentration to 1 mM. Likewise, 2.5 mg (0.01 mmol) of methylmercury chloride ($CH_3HgCl$) (CAS [115-09-3]; Catalog #: 33368 from Sigma Aldrich) is dissolved in 10 mL of methanol in a Class A 10 mL volumetric flask (Sigma Aldrich) to bring the concentration to 1 mM. These solutions are further diluted with the $Na_2B_4O_7$ buffer in order to mix with the cysteine/PB solutions and form the mercury-cysteine/PB complex.

Optimizing the Flurophore/Thiol Labeling Chemistry for Mercury

In order to overcome the limitations of the current on-chip detection methods for analysis of mercury speciation, our approach utilizes the formation of metal complexes in combination with fluorescent labeling for sensitive laser induced fluorescence (LIF) detection. Mercury has high affinity for thiol groups. For example, inorganic mercury ions ($Hg^{2+}$) and methylmercury ($CH_3Hg^+$) form complexes with thiols according to the reactions shown:

$Hg^{2+}+2\ RSH \rightarrow RS\text{—}Hg\text{—}SR+2\ H^+$

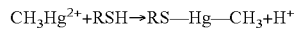

$CH_3Hg^{2+}+RSH \rightarrow RS\text{—}Hg\text{—}CH_3+H^+$

Our goal then is to find a thiol that can be conveniently tagged by a highly fluorescent probe while preserving mercury affinity to thiols.

Pacific Blue™ succinimidyl ester (PB) was selected as the fluorescent probe based on its high extinction coefficient (46,000 $cm^{-1}\ M^{-1}$) that enables low limits of detection of amino acids. FIG. 1 shows the reaction between PB and an amino acid. The highest labeling efficiency was obtained at pH~9, so for the work described here the reaction was performed in 10 mM Tetraborate buffer, pH 9.2.

Figure 2B:
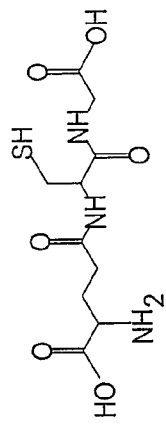
FIGS. 2(*a*) and 2(*b*) show the chemical structure of two possible thiol-containing amino acids (respectively, cysteine and glutathione) for use in the reaction in FIG. 1.
Figure 2A:
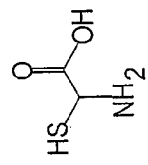

Two thiols that also contain amine groups were selected, cysteine and glutathione, as the amine group can be labeled with PB while the thiol group forms a complex with mercury species. FIG. 2 shows the molecular structure of glutathione and cysteine.

Reagents and Solutions

All chemicals were analytical reagent grade and used as received. Sodium tetraborate ($Na_2B_4O_7.10H_2O$) and sodium hydroxide were purchased from Fisher Scientific (Fair Lawn, N.J.). All aqueous solutions were prepared using 18 MΩ·cm water. The pH was adjusted using either 1M NaOH or 1M HCl (Sigma-Aldrich, St. Louis, Mo.) and measured using a glass electrode and a digital pH meter (Orion 290A, Thermo; Waltham, Mass.). L-cysteine and L-Glutathione reduced were purchased from Sigma-Aldrich (Saint Louis, Mo.). Pacific Blue succinimidyl ester (PB) was purchased from Invitrogen (Carlsbad, Calif.). Stock solutions of amino acids (10 mM in water) and Pacific Blue (20 mM in dimethylformamide (DMF)) were prepared and kept frozen (−20° C.) when not in use. The labeling reaction was performed off-chip by mixing amino acids and PB (200 M) and allowing the reaction to proceed for at least 1 hour. The reaction was performed in 10 mM tetraborate buffer, pH 9.2. Other amino acid solutions were prepared by diluting the corresponding amount of stock in buffer.

Microchip Capillary Electrophoresis

A LabSmith HVS448 High Voltage Sequencer (Livermore, Calif.) was used to control voltages applied to electrophoresis wells during injection (10 sec) and separation (250 sec). Laser-induced fluorescence detection was performed with a commercial Nikon Eclipse TE2000-U inverted microscope system. A 405 nm Melles Griot Diode Laser (CVI Melles Griot, Carlsbad, Calif.) was used for excitation, and emission was detected by a CCD camera (Cascade 650, Photometrics). All experiments were performed on a commercial microchip (Micralyne Inc., Edmonton, Canada). Devices were mounted inside a polycarbonate fixture designed in our laboratory. The separation channel was conditioned before use with 0.1M NaOH for 10 min, followed by water and buffer for 5 min each. During injection, 600, 900, 0, and 900 V were applied to buffer, sample, sample waste, and waste respectively. After 10 sec the potentials were switched to 3000, 1400, 1400, and −3000 V. Data were processed using PeakFit (Systat Software Inc., San Jose Calif.).

Optimization of Separation. Buffer

Figure 3:
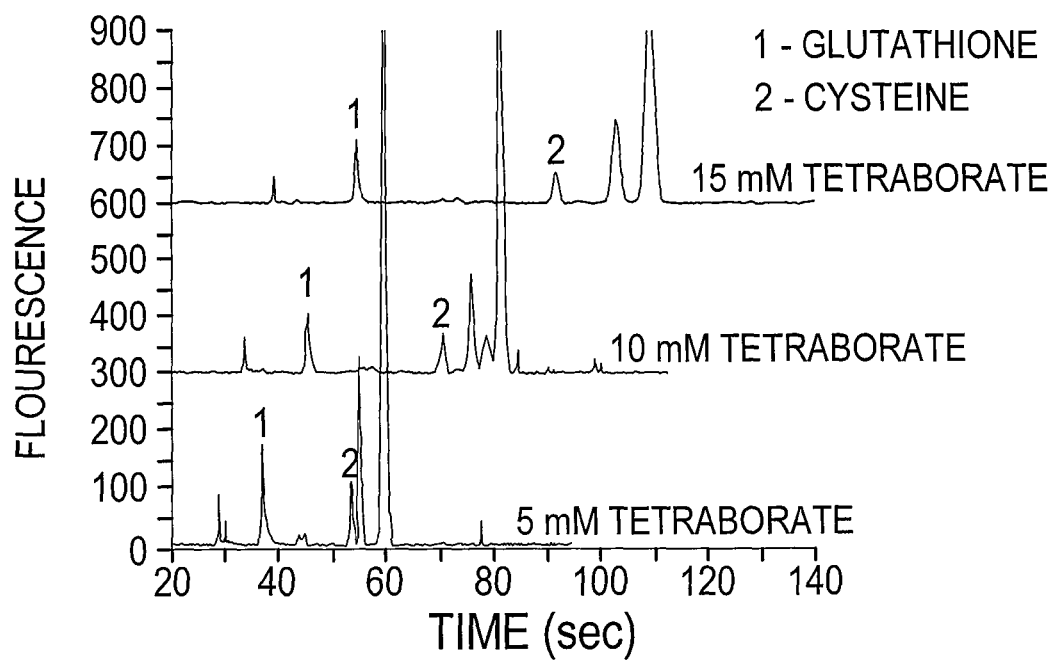
FIG. 3 are electropherogram graphs of fluorescence (RFU) over time (in seconds) of a mixture of glutathione and cysteine (200 nM each for separation buffer concentrations).
Figure 4:
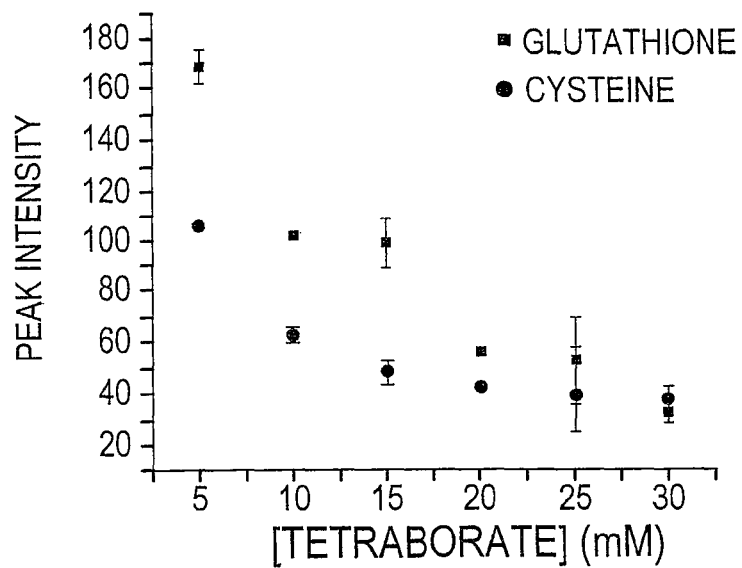
FIG. 4 is a graph of peak fluorescence intensity as a function of tetraborate separation buffer concentration (mM) under separation conditions of 9.2 pH and $V_{sep}$=6 kV.

In order to study the effect of buffer concentration on the separation of the selected thiols, electrolyte solutions ranging from 5 to 30 mM tetraborate (pH 9.2) were analyzed. FIG. 3 shows the electropherograms for 5, 10, and 15 mM buffer. FIG. 4 shows the peak intensity and resolution as a function of buffer concentration, respectively. As the buffer concentration increased, the migration times of all analytes increased while the peak intensities decreased. It is clear from this data that lower concentration of separation buffer would provide better sensitivity. The glutathione peak is well resolved for all low buffer concentrations but cysteine is too close to the dye peaks in the lowest concentration used. This could compromise the analysis of the mercury species once they react with the labeled cysteine and alter its mobility. Considering both, sensitivity and resolution, 10 mM tetraborate was selected as the optimal separation buffer concentration. It is worth mentioning that in the case of very dilute samples a lower concentration of buffer could be used to improve sensitivity.

Limit of Detection

Figure 5:
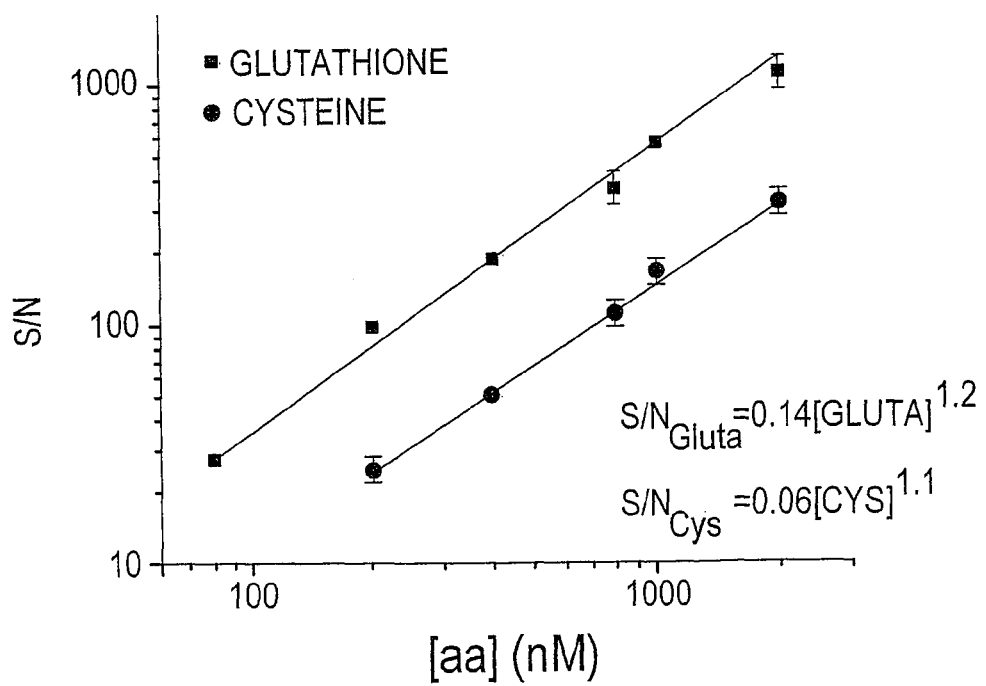
FIG. 5 is a graph of peak intensity signal-to-noise ratio (S/N) as a function of buffer concentration in the sample reservoir for glutathione and cysteine 200 nM under separation conditions of 25 mM tetraborate, 9.2 pH and $V_{sep}$=6 kV.

Using optimized conditions for labeling and separation, calibration curves (FIG. 5) and limits of detection were obtained for each thiol. Limits of detection in the low nM range were obtained for both compounds but glutathione provides a better sensitivity compared to cysteine. Limits of detection and correlation coefficient for each thiol are summarized in the following table:

| Thiol | Limit of Detection (nM) | $R^2$ |
|---|---|---|
| L-Cysteine | 32 ± 7 | 0.993 |
| L-Glutathione | 13 ± 2 | 0.976 |

The invention claimed is:

1. A method of using a fluorescent dye for measuring mercury concentration in a sample, comprising:
    combining a known quantity of a sample with a known quantity of a fluorophore of 6,8-difluoro-7-hydroxy-2-oxo-2H-chromene-3-carboxylate amide, wherein the amide contains a free thiol group, any mercury in the sample reacting with the fluorophore to form a mercury-fluorophore complex;
    illuminating the separated complex with a laser source to excite fluorescence; and
    measuring the fluorescence intensity as indicative a concentration of mercury in the sample, the mercury-fluorophore complex being distinguishable from remaining unreacted fluorophore by a different fluorescence wavelength.

2. The method as in claim 1 wherein fluorophore is buffered with sodium tetraborate to a pH in a range from 8.5 to 9.2 prior to combining with the sample.

3. The method as in claim 1 further comprising using a chromatography technique to pre-separate the sample constituents according to mercury species and to separate out any thiol-reacting metal species other than mercury, different species of mercury being detected by fluorescence in different time intervals.

4. The method as in claim 1, wherein the 6,8-difluoro-7-hydroxy-2-oxo-2H-chromene-3-carboxylate amide is formed from 6,8-difluoro-7-hydroxy-2-oxo-2H-chromene-3-carboxylate succinimidyl ester reacted with an amino acid so as to substitute the succinimide group with the amino acid.

5. The method as in claim 4, wherein the amino acid is cysteine.

6. The method as in claim 4, wherein the amino acid is glutathione.

* * * * *